United States Patent [19]
Rybarski

[11] Patent Number: 5,396,178
[45] Date of Patent: Mar. 7, 1995

[54] APPARATUS AND METHOD FOR DETERMINING THAT EQUIPMENT IS CLEAN

[75] Inventor: Robert J. Rybarski, Hebron, Ind.

[73] Assignee: Dober Chemical Corporation, Midlothian, Ill.

[21] Appl. No.: 884,023

[22] Filed: May 18, 1992

[51] Int. Cl.⁶ .............................................. G01N 27/06
[52] U.S. Cl. .................... 324/439; 340/603; 210/85; 134/113
[58] Field of Search ............... 324/439; 210/85, 86; 340/603; 134/113, 18

[56] References Cited

U.S. PATENT DOCUMENTS

| | | | |
|---|---|---|---|
| 3,276,458 | 10/1966 | Iversen et al. | |
| 3,595,252 | 7/1971 | Conte | 134/113 |
| 3,940,336 | 1/1976 | Macevicz et al. | |
| 3,973,572 | 8/1976 | Brous | |
| 3,990,066 | 11/1976 | Malmgren | 340/603 |
| 4,003,705 | 1/1977 | Buzza et al. | |
| 4,118,663 | 10/1978 | Barben, II | 324/439 |
| 4,303,887 | 12/1981 | Hill et al. | 324/441 |
| 4,515,641 | 5/1985 | Juenger | 134/113 |
| 4,563,272 | 1/1986 | Yoshida et al. | 210/93 |
| 4,587,518 | 5/1986 | King | 340/603 |
| 4,639,137 | 1/1987 | Hazan et al. | 134/113 |
| 4,662,133 | 11/1987 | Furuno | |
| 4,682,113 | 7/1987 | Barben, II | 324/439 |
| 4,731,154 | 3/1988 | Hausman Hazlitt et al. | 134/113 |
| 4,806,912 | 2/1989 | Clack | 340/603 |
| 4,872,356 | 10/1989 | Barnett et al. | |
| 4,915,119 | 4/1990 | Franklin | 134/94 |
| 4,937,557 | 6/1990 | Tucci et al. | 340/603 |
| 5,057,212 | 10/1991 | Burrows | 340/603 |
| 5,087,883 | 2/1992 | Hoffman | 340/603 |

FOREIGN PATENT DOCUMENTS 1124211  11/1984  U.S.S.R. .................... 324/439

*Primary Examiner*—Kenneth A. Wieder
*Assistant Examiner*—Glenn W. Brown
*Attorney, Agent, or Firm*—Frank J. Uxa

[57] ABSTRACT

Apparatus and methods for determining that a piece of equipment, for example, used in the biotechnology or pharmaceutical industries, is clean are disclosed. The invention involves measuring the electrical conductivity of an aqueous liquid medium both before and after the medium is used to contact, e.g., rinse, the piece of equipment. The equipment is determined to be clean when these two measured electrical conductivities are substantially equal.

20 Claims, 1 Drawing Sheet

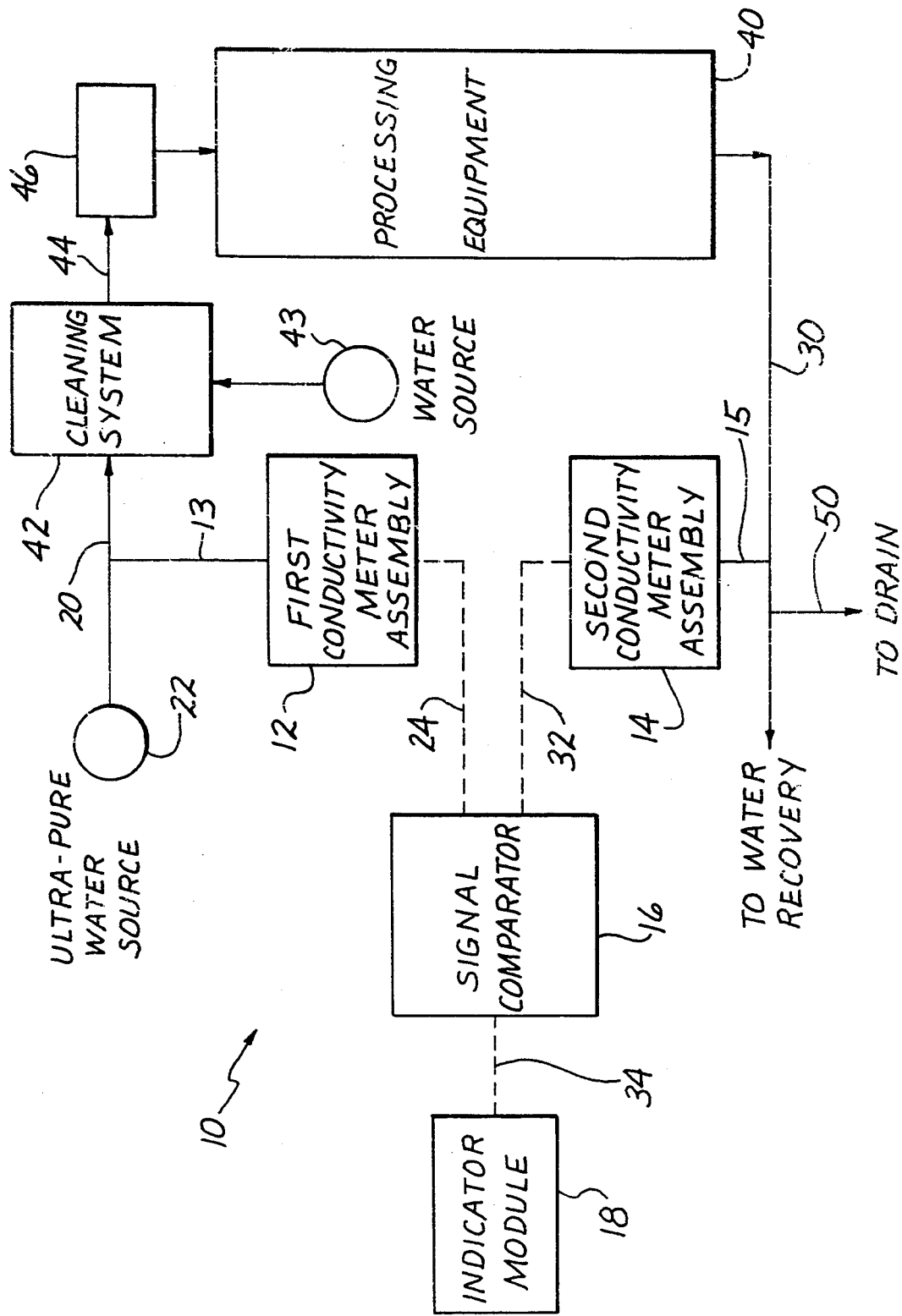

APPARATUS AND METHOD FOR DETERMINING THAT EQUIPMENT IS CLEAN

BACKGROUND OF THE INVENTION

The present invention relates to apparatus and methods for determining when equipment is clean. More particularly, the invention relates to such apparatus and methods which involve electrical conductivity measurements and which preferably provide a signal indicating that the equipment is clean.

Throughout the process industries, process effectiveness and efficiency often requires that equipment be maintained at a high degree of cleanliness. Thus, in many situations, pieces of equipment, such as processing vessels, heat exchangers, storage tanks, pipelines and the like, are subjected to regular and routine cleaning procedures to remove debris and/or contaminants from the equipment, for example, the internal components or surfaces of the equipment.

Quite often a visual inspection of the equipment after the cleaning procedure is sufficient to determine that the equipment is acceptably clean. However, there are instances where such a visual inspection is not a satisfactory indication of equipment cleanliness. Examples include equipment used in the biotechnology, pharmaceutical and related industries which are regulated at least to some extent by the U.S. Food and Drug Administration, hereinafter the FDA.

With regard to certain pieces of equipment, the FDA has mandated that the equipment pass a certain test before it is certified as being clean, and, therefore, ready or eligible to be employed or operated again, e.g., in a manufacturing process. In brief, this FDA mandated test requires that the equipment be subjected to rinsing with highly pure water, e.g., ultra-pure water. The electrical conductivity of the effluent rinse water is monitored. In order for the equipment to be certified clean in accordance with this test procedure, the electrical conductivity of the effluent rinse water must be at or below a predetermined value, for example, at or below 1.0 microsiemen per square cm.

One problem with this test is that it frequently provides false negative results, that is it frequently indicates that clean equipment is not clean. Such false negative results can lead to prolonged and unnecessary process downtime while the equipment is subjected to re-cleaning. An important reason or cause of this problem is believed to be the purity of the high purity rinse water itself, which often varies over a relatively wide range. Thus, in order to obtain certification that a piece of equipment is clean, it is often necessary to wait until the high purity rinse water has been sufficiently processed so as not to unduly contribute to the conductivity of the effluent rinse water. This, in turn, can result in processing delays and, ultimately, to increased manufacturing costs.

It would be advantageous to provide a new system for determining that a piece of equipment is clean.

SUMMARY OF THE INVENTION

New apparatus and methods for determining that a piece of equipment is clean have been discovered. The new system, unlike the above-noted test procedure, is not dependent on a specific degree of rinse water purity. Thus, one need not be concerned with maintaining the incoming rinse water absolutely pure, e.g., substantially no conductivity. The present system takes into account variations in incoming rinse water purity while, at the same time, providing an accurate and reliable indication that a piece of equipment is clean, for example, certifiably clean. The present apparatus and methods are relatively straightforward, can employ components which are commercially available, and are relatively easy to operate and practice. Ultimately, increased processing effectiveness and efficiency, and reduced manufacturing costs can be achieved.

In one broad aspect, the present methods for determining that a piece of equipment is clean comprise steps (a), (b), (c) and (d).

Step (a) involves causing an aqueous liquid medium, preferably having an electrical conductivity of less than about 5 or less than about 2.5 microsiemens per square cm and more preferably having been processed to provide ultra-pure water, to come into contact with, preferably to rinse, the piece of equipment. Step (b) provides for determining the electrical conductivity of the aqueous liquid medium prior to the medium being used in step (a). Step (c) provides for determining the electrical conductivity of the aqueous liquid medium after the medium is used in step (a). Step (d) involves comparing the electrical conductivities determined in steps (b) and (c). The piece of equipment is determined to be clean when the electrical conductivity determined in step (c) substantially equals the electrical conductivity determined in step (b). Preferably, the piece of equipment is determined to be clean when this substantial equality of electrical conductivities is maintained for a predetermined period of time, for example, on the order of about one minute or less to about 5 minutes or about 10 minutes or more.

This electrical conductivity match, as described herein, between the incoming rinse water and the effluent rinse water has been found to provide a very useful, accurate and reliable indication of the cleanliness of the piece of equipment. Thus, it is not necessary to maintain the incoming rinse water at a set purity level. Without this set purity constraint, the cleanliness of a piece of equipment can be more easily, rapidly and efficiently determined. Substantial cost savings and other processing economies are ultimately obtained.

In another broad aspect of the present invention, apparatus or systems for determining that a piece of equipment is clean are provided. Such apparatus or systems may be employed in practicing the present methods described herein.

In one embodiment, the present apparatus comprises a first conductivity meter assembly, a second conductivity meter assembly, and a signal comparing or comparator assembly. The first conductivity meter assembly is located with respect to the piece of equipment the cleanliness of which is to be determined to measure the electrical conductivity of an aqueous liquid medium prior to the medium being used to contact, preferably rinse, the piece of equipment. This first conductivity meter assembly provides a first signal indicative of the electrical conductivity measured at this point. The second conductivity meter assembly is located with respect to the piece of equipment to measure the electrical conductivity of the aqueous liquid medium after the medium is used to contact the equipment. This second conductivity meter assembly provides a second signal indicative of the electrical conductivity measured at this point. The signal comparing assembly is located so as to receive both the first signal and the second signal. This signal comparing assembly is structured to compare the first signal and the second signal and to provide a third signal when the electrical conductivity measured by the second conductivity meter assembly substantially equals the electrical conductivity measured by the first conductivity meter assembly.

The present apparatus are relatively simple in construction. For example, the meter assemblies used in the present systems may include conventional, well known and/or commercially available electrical conductivity meters and transmitters. The signal comparing assembly may include a digital computer and/or an analog computer, for example, a microprocessor, many of which are conventional and commercially available.

BRIEF DESCRIPTION OF THE DRAWINGS

The drawing is a schematic illustration of an embodiment of the present system.

DETAILED DESCRIPTION OF THE INVENTION

The present methods and systems for determining that a piece of equipment, for example, a piece of processing equipment as described herein, is clean, preferably certifiably clean, for example, in accordance with FDA regulations, are relatively straightforward and easy to operate and practice. Although the present methods and systems are useful with any piece of equipment, they are particularly useful in monitoring equipment used in the biotechnology, pharmaceutical and related industries in which equipment is to be very clean.

The present methods involve a series of steps. The present methods comprise steps (a), (b), (c) and (d). Step (a) involves causing an aqueous liquid medium to come into contact with, preferably to rinse, the piece of equipment which is to be determined to be clean. This step may be conducted in accordance with routine or standard practices involving water rinsing of the piece of equipment, for example, with ultra-pure water.

The aqueous liquid medium prior to being used to contact the equipment in step (a) preferably has an electrical conductivity of less than about 5 or less than about 2.5 microsiemens per square cm. In a particularly useful embodiment, this aqueous liquid medium is subjected to processing designed to produce ultra-pure water prior to being used to contact the equipment. Ultra-pure water has very much reduced electrical conductivity, for example, on the order of about 2.0 microsiemens per square cm or about 1.0 microsiemen per square cm or less. One important advantage of the present system is that the processing of the liquid aqueous medium to provide high purity water, for example, ultra-pure water, is not the determining factor in the present invention. Thus, as is often the case, the processing of the water to provide high purity water is such that the electrical conductivity of the final pure water product may vary over a relatively broad range, for example, between about 0.1 or 0.2 microsiemen per square cm to about 2.5 or about 5 microsiemens per square cm. The present invention takes into account these variations or at least provides a reliable indication of the cleanliness of a piece of equipment even though the electrical conductivity of the rinse water used varies from the specifications for ultra-pure water.

In accordance with step (b) of the present methods, the electrical conductivity of the aqueous liquid medium is determined prior to the aqueous medium being used to contact the piece of equipment. Further, in accordance with step (c) of the present methods, the electrical conductivity of the aqueous liquid medium after it is used to contact the piece of equipment is also determined. Any suitable electrical conductivity meter assembly or assemblies may be employed in the practice of these determining steps. Many such electrical conductivity meter assemblies are conventional, well known in the art, and commercially available. Examples of useful electrical conductivity meter assemblies include various sanitary probe-type conductivity meters coupled with transmitters, and the like, such as electrical conductivity meter/transmitter combinations sold by Sensor Development, Inc., Foxboro, and Rosemont Analytical.

Both influent (for step (b)) and effluent (for step (c)) electrical conductivity meter assemblies should be such that they can provide signals, e.g., electronic signals, indicative of the electrical conductivity measured. Preferably, each of the meter assemblies is structured so as to provide for continuous monitoring of the electrical conductivity of the aqueous liquid medium, for example, while aqueous liquid medium, e.g., ultra-pure water, is used to contact the piece of equipment.

The signals from the electrical conductivity meter assemblies are passed to the signal comparator assembly, for example, involving a digital computer and/or an analog computer. In step (d) of the present methods, the electrical conductivities determined in steps (b) and (c) are compared. The piece of equipment is determined to be clean when the electrical conductivity determined in step (c) equals the electrical conductivity determined in step (b). Preferably, the piece of equipment is determined to be clean when the two electrical conductivities are within at least about 0.2 or about 0.1 microsiemen per square cm. Further, it is preferred that this electrical conductivity match be maintained for a predetermined period of time, e.g., on the order of about 1 minute or about 5 minutes to about 10 minutes or longer, before the piece of equipment is determined to be clean.

This signal comparing or comparator assembly may be chosen from devices which are conventional, well known, and commercially available. A relatively simple signal comparing circuit is useful in the present system. Preferably, the signal comparator assembly functions automatically, i.e., without human intervention. This "automatic" feature increases the objectivity of the determination that the equipment is clean. Examples of useful signal comparator assemblies include microprocessors and the like, such as the microprocessors sold by Allen Bradley under the trademarks SLC-500 and PLC-5. Such microprocessors can be programmed, for example, using conventional and well known computer programming techniques and/or procedures, to function as the signal comparator assembly, as described herein.

A very useful additional feature of the present invention is that of providing a signal when the piece of equipment is determined to be clean. Thus, after the comparison of the electrical conductivities has determined that the piece of equipment is clean, the signal comparator assembly preferably provides an additional signal to an indicator assembly which, in response to this signal, provides an indication that the piece of equipment is clean. This indication may be an audible indication, a visual indication and/or a printed indication. Conventional equipment, such as an audible alarm, a cathode ray tube-based or light emitting dioxide-based or liquid crystal-based display module, or a printer may be employed in combination with the signal comparator assembly to provide the desired indication of cleanliness.

After the piece of equipment is determined to be clean, it may be employed in service, in particular, in the biotechnology industry or in the pharmaceutical industry.

The above-described methods for determining the cleanliness of a piece of equipment may be employed in conjunction with, or as part of, methods for cleaning the piece of equipment. In one embodiment, the present methods preferably further comprise treating the piece of equipment prior to performing the "cleanliness determining steps" described herein to remove debris and/or contaminants from the equipment. The treating step or steps can be conducted using conventional, well known and commercially available cleaning systems. A particularly useful example of such a system is that sold by Dober Chemical Corporation under the trademark Chematic CIP ®. Systems described in Franklin U.S. Pat. No. 4,915,119 are useful in treating pieces of process equipment in accordance with the present invention.

Referring now to the drawing, an embodiment of the present system, shown generally at 10, includes a first conductivity meter assembly 12, a second conductivity meter assembly 14, an automatic signal comparator 16 and an indicator module 18.

First conductivity meter assembly 12, a sanitary probe-type conductivity meter coupled with a transmitter of conventional design, measures the electrical conductivity of the water in line 20. First conductivity meter assembly 12 includes a first probe 13 which is introduced into line 20 and continuously monitors the electrical conductivity of the water therein. The water in line 20 comes from an ultra-pure water source 22. The first conductivity meter assembly 12 provides or transmits a signal through line 24 to signal comparator 16. The signal in line 24 is indicative of the electrical conductivity of the water in line 20.

The second conductivity meter assembly 14, a sanitary probe-type conductivity meter coupled with a transmitter of conventional design, measures the electrical conductivity of the water in line 30. Second conductivity meter 14 includes a second probe 15 which is introduced into line 30 and continuously monitors the electrical conductivity of the water therein. Second conductivity meter assembly 14 provides or transmits a signal through line 32 to signal comparator 16 which is indicative of the electrical conductivity of the water in line 30.

Signal comparator 16, a digital computer or microprocessor of conventional design, is programmed to receive the signals from lines 24 and 32 and to compare the values of these signals when the two signals are of substantially equal value, the signal comparator 16 activates a first timer located therein which runs until the signals in lines 24 and 32 no longer substantially match each other or until the expiration of a predetermined period of time from the time the substantial signal match first occurs, whichever event occurs first. If the predetermined period of time has not expired and the two signals no longer match each other, then the first timer is inactivated and returned to zero time and the signal comparator 16 continues to compare the signals from lines 24 and 32 until substantial equality is again achieved. Once substantial equality is achieved, the first timer is activated again.

This process is continued until the first timer is inactivated by the expiration of the above-noted predetermined period of time. Once this point is reached, a signal is provided by signal comparator 16 through line 34 to indicator module 18 which provides audible and printed indications that the signals from lines 24 and 32 have matched each other for the above-noted predetermined period of time, for example, for five minutes. The provision of such audible and printed indications is evidence that the equipment being tested is certifiably clean, as will become apparent hereinafter.

Processing equipment, shown schematically in the drawing at 40, is used in the pharmaceutical industry, for example, as a chemical reaction vessel. As commonly occurs, processing equipment 40 is routinely removed from service for cleaning.

A conventional cleaning system, shown schematically in the drawing at 42, provides various aqueous streams to processing equipment 40 through line 44, and spray nozzle assembly 46 (of conventional design) to remove debris and/or contaminants. For example, cleaning system 42 may provide an alkaline and/or acid cleaner and/or a sanitizer and/or a biocide, each of which is aqueous-based, to processing equipment 40 to clean processing equipment 40. The aqueous-based streams from cleaning system 42, which include water from water source 43, pass through processing equipment 40, into line 30 and then into line 50 to a drain for disposal. Alternately, the aqueous-based material in line 50 can be recovered and treated to make it more environmentally acceptable. In any event, after cleaning system 42 has been used on processing equipment 40, processing equipment 40 should be clean, for example, sufficiently clean to satisfy the regulations of the FDA.

The system 10 is designed to verify that processing equipment 40 is clean, preferably in accordance with FDA standards and regulations. Thus, after cleaning system 42 has been used to clean processing equipment 40, system 10 is employed.

When cleaning system 42 is in use, water is provided from water source 43 and no water from ultra-pure water source 22 is used. When system 10 is in use, water is provided from ultra-pure water source 22 and no water from water source 43 is used.

When system 10 is employed, water from ultra-pure water source 22 passes through line 20, cleaning system 42, line 44, and then through spray nozzle assembly 46 into processing equipment 40 and acts as a rinse for processing equipment 40. Water from processing equipment 40 passes through line 30 and into a water recovery system where the water is treated to provide ultra-pure water for reuse in the present system.

As the water from ultra-pure water source 22 passes through line 20 and into processing equipment 40, system 10 is activated. First conductivity meter assembly 12 continuously monitors the electrical conductivity of the water in line 20 and passes a signal through line 24 to signal comparator 16 which is indicative of this electrical conductivity. Similarly, second conductivity meter assembly 14 continuously monitors the electrical conductivity of the water in line 30 and passes a signal through line 32 to signal comparator 16 which is indicative of this electrical conductivity.

This process continues until signal comparator 16 provides a signal through line 34 to indicator module 18, and an audible indication and a printed indication are provided by indicator module 18 in response to the receipt of the signal from line 34. Indicator module 18 includes an alarm horn (of conventional design, for providing the audible indication) and a printer (of conventional design, for providing the printed indication), each of which is activated by the signal from line 34 to provide an indication. The provision of these indications means that the processing equipment 40 is clean, preferably certifiably clean in accordance with the FDA regulations.

The signal comparator 16 is provided with a second timer which begins running when the system 10 is activated or when the first conductivity meter assembly 12 starts providing a signal through line 24. This second timer continues to run regardless of the condition of the match of signals from lines 24 and 32. If the second timer runs for more than a second predetermined period of time, for example, for more than one hour, before the indications are provided by indicator module 18, the operator of the system 10 is notified of this passage of time, for example, by another indication provided by indicator module 18 in response to another signal passed from signal comparator 16 through line 34. The fact that this second predetermined period of time has passed without the desired conductivity match being obtained is evidence that the processing equipment 40 may, in fact, not be clean. In this situation, system 10 may be inactivated, the flow of ultra-pure water stopped, and cleaning system 42 again used to clean processing equipment 40. After this recleaning, the flow of ultra-pure water through processing equipment 40 is again started and the system 10 is again activated to determine if processing equipment 40 is clean. This cycle may be repeated until processing equipment 40 is determined to be clean by system 10.

The present invention effectively and efficiently provides an objective and reliable determination that a piece of equipment is clean, for example, certifiably clean sufficiently to conform to FDA, or other stringent, regulations or standards. Importantly, the present methods and systems are not dependent on the absolute purity of the high purity water employed in the cleanliness determination. Thus, the purity of this high purity water can vary over a relatively wide range without substantially affecting the accuracy of the cleanliness determination. The present invention allows one to determine equipment cleanliness without being overly concerned with the purity of the high purity water, for example, without waiting until the high purity water meets ultra-pure water specifications. Being able to determine equipment cleanliness without being constrained by the need for on-spec ultra-pure water allows one to reduce equipment downtime and, ultimately, to reduce operating costs.

While this invention has been described with respect to various specific examples and embodiments, it is to be understood that the invention is not limited thereto and that it can be variously practiced within the scope of the following claims.

What is claimed is:

1. A method for determining that a piece of equipment is clean which comprises:
   (a) causing an aqueous liquid rinse medium to come into contact with said piece of equipment;
   (b) determining the electrical conductivity of said aqueous liquid medium prior to said aqueous liquid rinse medium being used in step (a);
   (c) determining the electrical conductivity of said aqueous liquid rinse medium after said aqueous liquid rinse medium is used in step (a); and
   (d) comparing the electrical conductivities determined in steps (b) and (c), said piece of equipment being determined to be clean when said electrical conductivity determined in step (c) substantially equals said electrical conductivity determined in step (b).

2. The method of claim 1 wherein said aqueous liquid rinse medium prior to being used in step (a) has an electrical conductivity of less than about 5 microsiemens per square cm.

3. The method of claim 1 wherein steps (b), (c) and (d) are performed substantially continuously while step (a) is being performed.

4. The method of claim 3 wherein said piece of equipment is determined to be clean when said electrical conductivity determined in step (c) substantially equals said electrical conductivity determined in step (b) for a predetermined period of time.

5. The method of claim 3 wherein said piece of equipment is determined to be clean when said electrical conductivity determined in step (c) is within at least about 0.1 microsiemen per square cm of said electrical conductivity determined in step (b).

6. The method of claim 1 wherein said piece of equipment is determined to be clean when said electrical conductivity determined in step (c) substantially equals said electrical conductivity determined in step (b) for a predetermined period of time.

7. The method of claim 1 wherein said piece of equipment is determined to be clean when said electrical conductivity determined in step (c) is within at least about 0.1 microsiemen per square cm of said electrical conductivity determined in step (b).

8. The method of claim 1 which further comprises treating said piece of equipment prior to performing step (a) to remove debris or contaminants from said piece of equipment.

9. The method of claim 1 which further comprises providing a signal when said piece of equipment is determined to be clean.

10. The method of claim 1 which further comprises employing said piece of equipment in the biotechnology industry or in the pharmaceutical industry after being determined to be clean.

11. An apparatus for determining that a piece of equipment is clean which comprises:
   a first conductivity meter assembly located with respect to the piece of equipment to measure the electrical conductivity of an aqueous liquid rinse medium prior to the aqueous liquid rinse medium being used to contact the piece of equipment and to provide a first signal indicative of said electrical conductivity measured by said first conductivity meter assembly;
   a second conductivity meter assembly located with respect to the piece of equipment to measure the electrical conductivity of the aqueous liquid rinse medium after the aqueous liquid rinse medium is used to contact the piece of equipment and to provide a second signal indicative of said electrical conductivity measured by said second conductivity meter assembly; and
   a signal comparing assembly located so as to receive both said first signal and said second signal, said signal comparing assembly being structured to compare said first signal and said second signal and to provide a third signal when said electrical conductivity measured by said second conductivity meter assembly substantially equals said electrical conductivity measured by said first conductivity meter assembly, said third signal being indicative that said piece of equipment is clean.

12. The apparatus of claim 11 wherein said signal comparing assembly is structured to operate automatically.

13. The apparatus of claim 11 wherein both said first conductivity meter assembly and said second conductivity meter assembly are structured to substantially continuously measure the electrical conductivity of the aqueous liquid rinse medium while the aqueous liquid rinse medium is contacting the piece of equipment.

14. The apparatus of claim 13 wherein said signal comparing assembly is structured to provide said third signal when said electrical conductivity measured by said second conductivity meter assembly substantially equals said electrical conductivity measured by said first conductivity meter assembly for a predetermined period of time.

15. The apparatus of claim 11 wherein said signal comparing assembly is structured to provide said third signal when said electrical conductivity measured by said second conductivity meter assembly substantially equals said electrical conductivity measured by said first conductivity meter assembly for a predetermined period of time.

16. The apparatus of claim 15 wherein said third signal is provided when said electrical conductivity measured by said second conductivity meter assembly is within at least about 0.1 microsiemen per square cm of said electrical conductivity measured by said first conductivity meter assembly for a predetermined period of time.

17. The apparatus of claim 11 which further comprises an indicator assembly located so as to received said third signal and structured so as to provide an indication of the receipt of said third signal.

18. The apparatus of claim 17 wherein said indication is one or more of the following: an audible indication, a visual indication or a printed indicator.

19. The apparatus of claim 11 wherein said signal comparing assembly comprises a digital computer or an analog computer.

20. The apparatus of claim 11 wherein said third signal is provided when said electrical conductivity measured by said second conductivity meter assembly is within at least about 0.1 microsiemen per square cm of said electrical conductivity measured by said first conductivity meter assembly.

* * * * *

UNITED STATES PATENT AND TRADEMARK OFFICE
CERTIFICATE OF CORRECTION

PATENT NO. : 5,396,178
DATED : March 7, 1995
INVENTOR(S) : Rybarski et al

It is certified that error appears in the above-indentified patent and that said Letters Patent is hereby corrected as shown below:

On the title page, item [75],
   add the inventors to "Daniel J. Dobrez, Homewood, Ill., and Robert J. Rybarski, Hebron, Ind."

Signed and Sealed this

Twenty-fifth Day of February, 1997

*Attest:*

BRUCE LEHMAN

*Attesting Officer*     *Commissioner of Patents and Trademarks*